(12) United States Patent
Julian et al.

(10) Patent No.: US 10,327,977 B2
(45) Date of Patent: Jun. 25, 2019

(54) DUAL DENSITY PRESSURE PAD

(71) Applicant: 3M INNOVATIVE PROPERTIES COMPANY, St. Paul, MN (US)

(72) Inventors: Dominic J. Julian, Loveland, OH (US); Jeremy J. Jacobs, Elsmere, KY (US)

(73) Assignee: 3M Innovative Properties Company, St. Paul, MN (US)

( * ) Notice: Subject to any disclaimer, the term of this patent is extended or adjusted under 35 U.S.C. 154(b) by 595 days.

(21) Appl. No.: 14/406,793

(22) PCT Filed: Jun. 10, 2013

(86) PCT No.: PCT/US2013/045004
§ 371 (c)(1),
(2) Date: Dec. 10, 2014

(87) PCT Pub. No.: WO2013/191951
PCT Pub. Date: Dec. 27, 2013

(65) Prior Publication Data
US 2015/0182409 A1 Jul. 2, 2015

Related U.S. Application Data

(60) Provisional application No. 61/782,091, filed on Mar. 14, 2013, provisional application No. 61/661,338, filed on Jun. 18, 2012.

(51) Int. Cl.
*A61H 1/00* (2006.01)
*A61H 7/00* (2006.01)
(Continued)

(52) U.S. Cl.
CPC ....... *A61H 7/001* (2013.01); *A61F 13/00029* (2013.01); *A61F 13/06* (2013.01);
(Continued)

(58) Field of Classification Search
CPC ........ A61F 13/06; A61F 13/061; A61F 13/10; A61F 13/101; A61F 13/102; A61F 13/062; A61H 7/001; A61H 2001/16
See application file for complete search history.

(56) References Cited

U.S. PATENT DOCUMENTS

| | | |
|---|---|---|
| 4,370,978 A | 2/1983 | Palumbo |
| 4,716,898 A | 1/1988 | Chauve |

(Continued)

FOREIGN PATENT DOCUMENTS

| | | |
|---|---|---|
| CN | 201157520 | 12/2008 |
| JP | 2002-291956 | 10/2002 |

(Continued)

OTHER PUBLICATIONS

International Search Report for PCT International Application No. PCT/US2013/045004 dated Sep. 9, 2013, 3 pages.

*Primary Examiner* — Alexander J Orkin
(74) *Attorney, Agent, or Firm* — Ann K. Gallagher

(57) ABSTRACT

Provided are orthopedic, dual density pressure pads designed to transfer pressure onto a focused anatomical structure; typically through the assistance of a device that applies a perpendicular or downward force. The pad includes an outer layer including a relatively soft material and an interior support including a rigid material, with the interior support typically having a substantially greater hardness than the outer layer.

20 Claims, 3 Drawing Sheets

(51) Int. Cl.
*A61F 13/00* (2006.01)
*A61F 13/06* (2006.01)
*A61F 13/10* (2006.01)

(52) U.S. Cl.
CPC ..... *A61F 13/10* (2013.01); *A61F 2013/00174* (2013.01); *A61F 2013/00272* (2013.01); *A61F 2013/00617* (2013.01); *A61H 2201/16* (2013.01)

(56) References Cited

U.S. PATENT DOCUMENTS

| | | | |
|---|---|---|---|
| 4,991,573 A | 2/1991 | Miller | |
| 5,865,782 A | 2/1999 | Fareed | |
| 6,077,242 A | 6/2000 | Falk | |
| 6,080,124 A | 6/2000 | Falk | |
| 6,149,616 A * | 11/2000 | Szlema | A61F 13/061 602/26 |
| 6,485,448 B2 | 11/2002 | Lamping | |
| 6,641,549 B2 | 11/2003 | Darcey | |
| 6,755,800 B2 | 6/2004 | Weaver, II | |
| 7,637,883 B2 * | 12/2009 | Nyi | A61F 5/30 602/20 |
| 7,740,645 B2 * | 6/2010 | Babaev | A61B 17/1325 601/134 |
| D706,429 S | 6/2014 | Julian | |
| D706,938 S | 6/2014 | Weaver, II | |
| D706,939 S | 6/2014 | Weaver, II | |
| D706,940 S | 6/2014 | Julian | |
| 2007/0169378 A1 | 7/2007 | Sodeberg | |
| 2008/0066272 A1 | 3/2008 | Hammerslag | |
| 2012/0253252 A1 | 10/2012 | Weaver, II | |

FOREIGN PATENT DOCUMENTS

| | | |
|---|---|---|
| JP | 2005-281935 | 10/2005 |
| JP | 3921672 | 5/2007 |
| WO | 2012-003396 | 1/2012 |
| WO | 2012-030714 | 3/2012 |

* cited by examiner

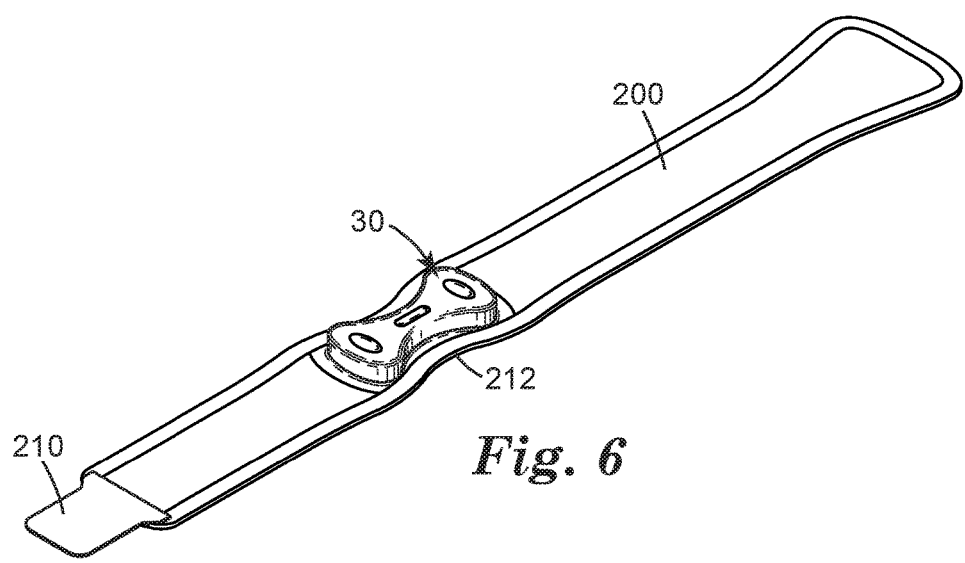

ns/045004, filed Jun. 10, 2013, which
DUAL DENSITY PRESSURE PAD

CROSS REFERENCE TO RELATED APPLICATIONS

This application is a national stage filing under 35 U.S.C. 371 of PCT/US2013/045004, filed Jun. 10, 2013, which claims priority to Provisional Application No. 61/661,338, filed Jun. 18, 2012 and Provisional Application No. 61/782,091, filed Mar. 14, 2013, the disclosure of which is incorporated by reference in its/their entirety herein.

BACKGROUND

This disclosure pertains to a pressure pad for use in orthopedic devices having a raised portion, and one or more protrusions that project from the raised portion. A wide variety of externally applied supports and joint-immobilizing braces are known to protect healthy and injured joints and to promote healing of certain injuries. Supports and braces are commonly used for injuries and other medical problems at the knee, thighs, elbow, waist, wrist and back. Certain products treat such injuries or medical problems by applying direct pressure to anatomy such as a tendon. These products generally have a pad or cushion to transfer force and provide direct pressure. These pads generally are either constructed of rigid materials or soft materials.

SUMMARY

The rigid materials used in pressure pads tend to create discomfort as they typically do not conform to anatomical contours, and can accordingly be uncomfortable to experience. During a typical muscle flexion state, the rigid materials tend to create a spike in reactive force. Conversely, pads including soft materials tend to compress easily distributing force over a larger area and decreasing the effectiveness of the direct force. Additionally, broadly distributed force may necessitate additional force requirements to be provided by a strap or other pressure device which can also lead to discomfort, or possibly cut off circulation.

The present disclosure provides an orthopedic, dual density pad designed to transfer pressure onto an anatomical structure, typically through the assistance of some form of device that applies perpendicular or downward force. The pad includes an outer layer including a soft material and a second interior support structure including a rigid material, with the interior support structure typically having a substantially greater Shore A hardness than the outer layer. The pad contours at least portions of an anatomical structure to both create localized pressure as well as distributed force. The use of multiple material densities allows for force dissipation, which can improve comfort when a user's muscles are in flexion.

In one aspect, the present disclosure provide a pressure pad for transferring pressure to an anatomical structure, the pad comprising a base; an interior support comprising a rigid material coupled to the base; a body including a soft material projecting outwardly from the base and at least partially enveloping the interior support; a protrusion extending outwardly from the body, wherein at least one geometric feature of the protrusion corresponds to at least one geometric feature of the interior support.

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As recited herein, all numbers should be considered modified by the term "about".

As used herein, "a," "an," "the," "at least one," and "one or more" are used interchangeably. Thus, for example, a pressure pad comprising "a" protrusion can be interpreted as a pressure pad comprising "one or more" protrusions.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present disclosure is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exhaustive list.

BRIEF DESCRIPTION OF THE DRAWINGS

The invention will be further described with reference to the drawings, wherein corresponding reference characters indicate corresponding parts throughout the several views, and wherein:

FIG. 6 is a side view of the pressure pad of FIG. 4 coupled to an orthopedic support device.

Layers in certain depicted embodiments are for illustrative purposes only and are not intended to absolutely define the thickness, relative or otherwise, or the location of any component. While the above-identified figures set forth several embodiments of the invention, other embodiments are also contemplated, as noted in the description. In all cases, this disclosure presents the invention by way of representation and not limitation. It should be understood that numerous other modifications and embodiments can be devised by those skilled in the art, which fall within the scope and spirit of the principles of the invention.

DETAILED DESCRIPTION OF ILLUSTRATIVE EMBODIMENTS

Figure 1:
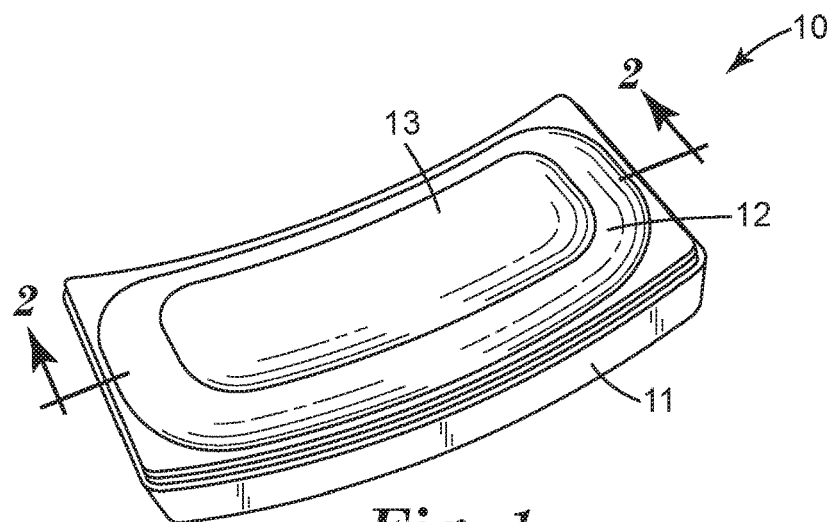
FIG. 1 depicts a perspective view of an orthopedic pressure pad according to one implementation of the disclosure.
Figure 2A:
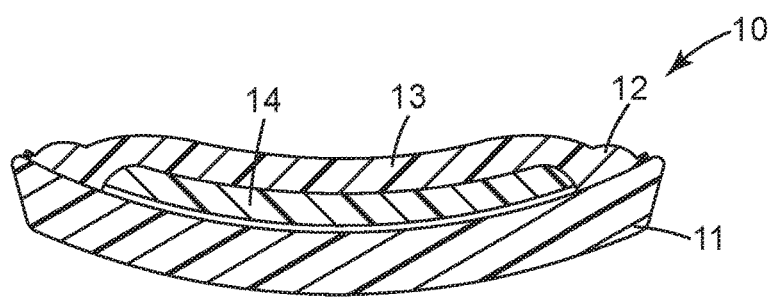
FIG. 2 is a cross-sectional view of the pressure pad of FIG. 1.
Figure 2B:
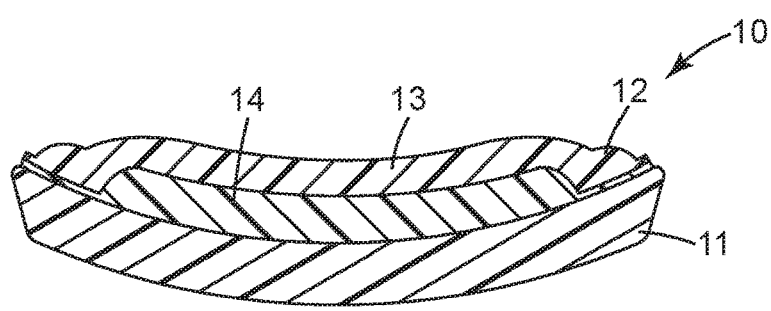

FIG. 1 depicts an implementation of a pressure pad 10 that is generally oval in shape, comprises a pad base 11, a raised body portion 12 that projects from the pad base 11, and a protrusion 13 that projects substantially about the center from the raised portion 12. Although, FIG. 1 shows the pad base 11, raised portion 12 and protrusion 13 substantially in the shape of an oval, these elements of the pressure pad 10 may be configured in any geometrical shape or combination of geometrical shapes, such as circular, square, rectangular, triangular, trapezoidal and the like, or combinations thereof, without deviating from the scope of the disclosure. The design of the raised portion 12 can, in certain implementations, offer a perpendicular, straight-line pressure (compression) both localized and distributed across a portion of the anatomy (e.g., a tendon located proximate the elbow). The configuration of the protrusion projecting substantially about the center from the raised portion 12 provides for the protrusion 13 to apply a focused pressure against a portion of the anatomy.

The pad 10 is typically designed to contour the curvature of a portion of a wearer's anatomy such as, for example, at least a portion of the wearer's elbow or knee. The pad 10 can be, as depicted in FIG. 1, a truncated, concave semicircle, with the protrusion 13 on the interior of the curve. The radius of curvature can vary depending upon the appendage on which the device will be worn (e.g., leg or arm) and the location on the appendage. The curvature can be tailored to provide comfort to a user when worn under compression, as well as distribute or localize forces depending on the condition being treated. It should be noted that the pressure pads of the disclosure can be used on multiple areas of anatomy and in myriad orthopedic support, brace, and pressure device. Any reference to applying pressure to an appendage, including joints, should not be interpreted to limit the scope or usefulness of the present disclosure.

The pad base 11 is generally made from a semi-rigid or non-stretch material. It may comprise a semi-rigid or rigid polymer such as nylon, polyoxymethylene (POM or "acetal"), polyethylene, polypropylene, acrylonitrile butadiene styrene (ABS), or the like. The pad 10 further includes an interior support 14 disposed proximate and underneath the protrusion 13. The interior support 14 comprises at least a portion of the interior of the pad 10. In certain embodiments, the interior support 14 includes a single structure having the same or substantially similar dimensions and/or geometry as the protrusion 13. In other aspects, the interior support 14 may include a plurality of structures (See, for example, FIG. 5) The interior support 14 preferably comprises a rigid material and has Shore A hardness greater than 70. In certain embodiments, the interior support 14 comprises a rigid material and has a Shore A hardness greater than 80. In particularly preferred implementations, the interior support 14 comprises a rigid material and has a Shore A hardness greater than 90. When measured according to a Shore D hardness scale, the interior support 14 typically has a hardness of at least 35 and no greater than 80. In other embodiments, the interior support 14 has a Shore D hardness of at least 50 and no greater than 75. In other embodiments, the interior support has a Shore D hardness of at least 45.

The interior support 14 can be molded into the base or made integral with the pad base 11. In certain other implementations, the interior support 14 includes the same material as the base 11, but is created separately. In other implementations, the interior support 14 comprises a different material (typically as rigid or more rigid) than the base 11. The interior support 14 can be coupled to a surface of the pad base by any known fixation mechanism, including welding and adhesion, for example. To increase potential user comfort, the interior support 14 is typically enveloped by an outer, soft layer, which forms the raised portion 12 and the protrusion 13. In other implementations, at least a portion of the interior support 14 is exposed or otherwise forms an exterior surface of the pad 10.

In other implementations, the interior support 14 is not fixed relative to the base 11. The interior support 14 can be at least partially enveloped by the soft compressible material described below, such that the interior support 14 "floats" in said the soft material (i.e., soft material exists in the space between the base 11 and a surface of the support 14 opposite the raised portion). These constructions allow for the support 14 to act as one or more pellets embedded in defined locations in the soft material. In other embodiments, the interior support 14 rests on, but is not otherwise coupled to, the base 11.

As one skilled in the art can appreciate, the height (as well as other dimensions) of the interior support 14 relative to the base can influence the hardness and attendant resistance to compression. In some embodiments, the interior support 14 is at least 50 thousandths of an inch. In other embodiments, the interior support 14 comprises a height of at least 10 hundredths of an inch. In other implementations, the interior support 14 comprises a height of no greater than one-half an inch.

The raised portion 12 and protrusion 13 are typically formed from soft compressible material, such as a thermoplastic elastomer (TPE), disposed on or molded onto a portion of the pad base 11 and the interior support 14. In addition to TPE, the raised portion 12 and protrusion 13 may be made from other compressible material such as gel, foam (e.g., urethane foam), thin or viscous liquid, gas, particulate and the like or combinations of such materials. This soft, outer layer typically has a uniform thickness in regions enveloping the interior support 14. The raised portion 12 and protrusion 13 preferably comprise a soft material having a Shore A hardness of at least 6. In certain embodiments, the raised portion 12 and protrusion 13 preferably comprise a Shore A hardness of at least 7. In particularly preferred implementations, the raised portion 12 and protrusion 13 comprise a Shore A hardness of at least 8.

The raised portion 12 and protrusion 13 preferably have a Shore A hardness of no greater than 35. In certain embodiments, the raised portion 12 and protrusion 13 preferably have a Shore A hardness of no greater than 30. In particularly preferred implementations, the raised portion 12 and protrusion 13 preferably have a Shore A hardness of no greater than 28. In certain particularly useful implementations, the Shore A hardness of the raised portion 12 and the protrusion 13 is at least 8 and no greater than 30.

In use, the interior support 14 will not initially deflect or compress under higher force as it is increasingly applied, by virtue of its greater Shore A (or Shore D) hardness. This resistance to compression of the interior support 14 may allow for increased localized pressure underneath soft outer layer of body 12 and protrusion 13. The flexible material of the raised portion 12 and protrusion 13 conforms to anatomical structures and promote anatomical conformance and comfort, thus allowing for dispersed pressure and higher distributed forces while mitigating discomfort as more force is applied. The pressure pads of the present disclosure will typically generate a linear deflection curve as greater force is applied. Accordingly, the pad will allow for flexion in the muscle while preventing or reducing the sharp pain caused by more rigid padding or spikes in reactive forces typical of more rigid pads.

Figure 3:
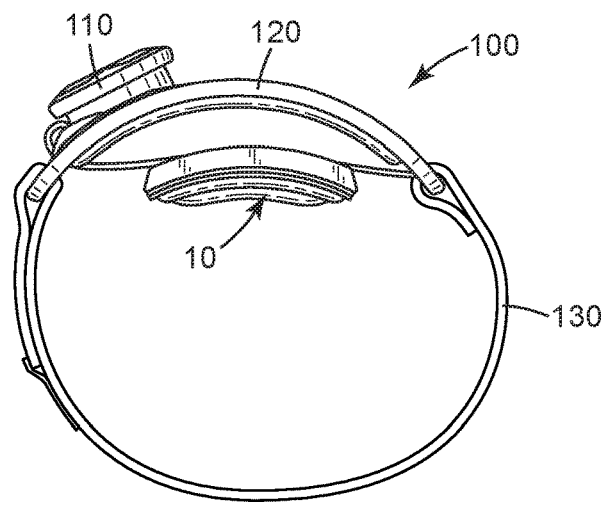
FIG. 3 is a side view of the pressure pad of FIG. 1 coupled to an orthopedic pressure device.

FIG. 3 depicts an exemplary device for applying perpendicular or downward force suitable for use with the pressure pads of the disclosure. The orthopedic pressure device 100 includes a main body 120 configured to contour the curvature of a portion of a wearer's anatomy. An adjustable strap 130 is coupled to the body 120 and is releasably engagable with the appendage. The strap 130 typically comprises a flexible belt that can be wrapped around the appendage and secured. The strap typically includes a relatively inelastic material (for example, a material having no more than about 30% stretch under tension) such as foam laminates (for example, a laminate including polyester inner layer, urethane foam, and nylon jersey for exterior durability) or a woven cotton or nylon strap. The strap 130 may also comprise an engaging surface similar, for example, to loop in a "hook and loop application" applied to either or both sides of the strap. The strap should be long enough to reach securely around the appendage and is preferably wide enough to permit comfortable wear. The width of the strap can help to distribute the applied circumferential force around the wearer's appendage so the device held on firmly but still comfortable.

The pressure device 100 includes a displacing mechanism 110 for applying perpendicular pressure to an appendage via the pressure pad 10. As depicted in FIG. 3, the displacing mechanism includes a lace and tensioning system for adjusting the perpendicular forces. Other displacing mechanisms are possible, including those described in US Patent Publication No. 2007/0169378. The tensioning system 110 includes a lace or cable that is threaded through or otherwise attached to a portion of the pad and body. The lace or cable is attached at opposite ends to a tightening or tensioning mechanism. In general, the tensioning mechanism comprises a control such as a lever, crank or knob, which can be manipulated to retract the lace. The displacing mechanism 110 uses line tension for displacing pad 10. If an opposing force is greater than the tension applied, the displacing mechanism 110 will "give" or be allowed to lose vertical displacement.

In use, the device is positioned on the wearer (e.g., a human or animal patient) such that area of the pressure pad 10 that provides perpendicular force is aligned over the soft tissues to be compressed. The adjustable strap 130 is then tensioned or engaged according to the patient's comfort, thereby securing the device onto the appendage of the wearer. The tensioning mechanism 110 is then used to tighten the lace and provide adjustable perpendicular force to the soft tissues. The wearer can continue to tighten the lace until the desired compression has been obtained. Thereafter, the wearer can use the adjustable tensioning mechanism 110 to increase or decrease compression at any time without the need to disengage the strap or connectors. Additional details regarding an orthopedic pressure device may be found in co-pending International Application No. PCT/US2012/030714, filed on Mar. 27, 2012 and entitled ORTHOPEDIC PRESSURE DEVICE. Other suitable orthopedic force delivery devices may be found in U.S. Pat. No. 6,755,800 to Weaver et al and U.S. Pat. No. 6,485,448 to Lamping et al.

Figure 4:
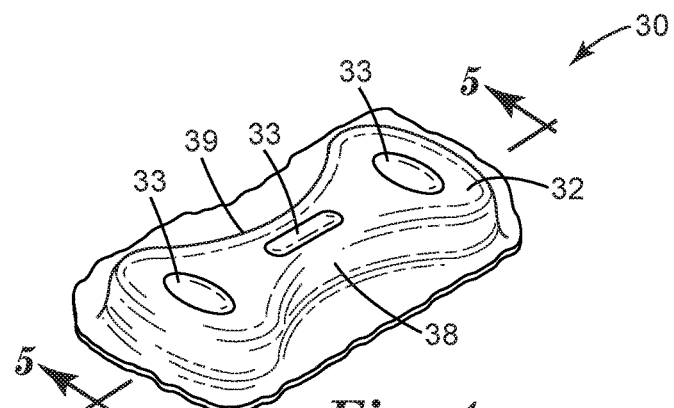
FIG. 4 depicts a perspective view of an orthopedic pressure pad according to another implementation of the disclosure.

FIG. 4 depicts another implementation of an orthopedic pressure pad 30. The pressure pad 30 includes a body projecting from a pad base. The body 32 includes anatomy contacting protrusions 33, which project outwardly from the exterior surface of the body 32. As depicted, the body 32 includes concave surfaces 38 and 39, such that the body 32 resembles a bow tie. The pressure pad 30, including the body 32 and any protrusions, may be configured in any geometrical shape or combination of geometrical shapes, such as circular, square, rectangular, triangular, trapezoidal and the like, or combinations thereof. It may be preferred that the anatomy contacting surfaces of the pad 30 (including the body and the protrusions) are rounded or softened for comfort under compression.

Figure 5:
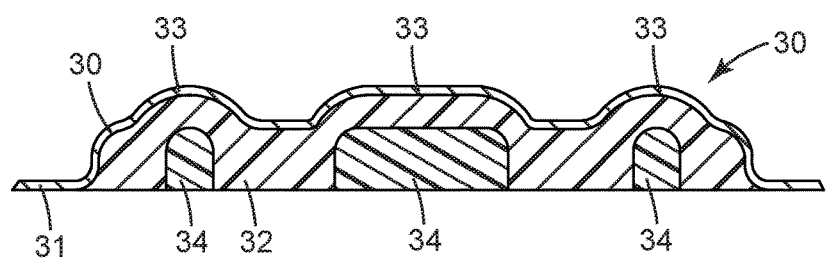
FIG. 5 is a cross-sectional view of the pressure pad of FIG. 4.

As can be appreciated by reference to FIG. 5, the location and orientation of the anatomy contacting protrusions 33 correspond to the same characteristics of the interior supports 34. The interior supports 34 can be molded to or otherwise integral with the base 31, or can be dispersed in the soft outer layer. The shape of the anatomy contacting protrusions substantially corresponds to the shape of the underlying or embedded support. Examples of suitable interior support shapes can include, but are not limited to, a variety of polyhedral shapes, parallelepipeds, prismatoids, prismoids, etc., and combinations thereof. For example, the features can be polyhedral, conical, frusto-conical, pyramidal, frusto-pyramidal, spherical, partially spherical, hemispherical, ellipsoidal, dome-shaped, cylindrical, and combinations thereof.

The interior supports 34 in FIG. 5 include a rounded, rail-like shape. The central support, and thus the central protrusion, is oriented along a different axis than either of the peripheral supports/protrusions. The central support extends along a first reference axis. The peripheral supports extend along a second reference axis that is perpendicular to the first reference axis. Accordingly, in certain implementations wherein the pad 30 is used to apply pressure to the knee, the central support can provide higher direct force to the patella or patellar tendon, while the peripheral supports can stabilize knee cap tracking.

As depicted, each of the interior supports 34 comprises the same height. It can be preferred, in certain circumstances, to have the central support at a slightly greater height than either peripheral support. Other permutations of differing height amongst the supports are also contemplated.

The interior supports 34 can comprise the same rigid materials as interior support 14 above. The supports may each comprise the same or different material. A soft outer layer (such as TPE, silicone, or other materials suitable for raised projection 12 above) is disposed above (and potentially below) each of the supports 34. Due to the space between the supports 34, the soft layer extends to the base. This configuration creates supported regions of the soft layer (i.e., the protrusions) and unsupported regions. The inclusion of supported regions proximate unsupported regions allows for the pad to transfer higher localized force in use, while the unsupported regions conform to and provide comfort for the user.

As can be appreciated, the location, dimensions, and geometry of the interior support(s) can affect the amount of force that can be absorbed by the pad. These aspects can be customized or otherwise designed as needed depending on the condition to be treated and the expected anatomical contact. For example, for Lateral/Medial Epicondylities, the interior support material may be selected to so that is absorbs a higher level of muscle flexion.

A support strap 200 including the pad 30 is depicted in FIG. 6. The strap typically comprises a relatively non-elastic material (for example, a material having no more than about 30% stretch under tension) such as foam laminates (for example, a laminate including polyester inner layer, urethane foam, and nylon jersey for exterior durability) or a woven cotton or nylon strap. The strap 200 can include concave portions 212 corresponding to the concave portions 38, 39 on the pressure pad 30. The corresponding concave portions 212 can guard against unwanted strap material being caught between the pad 30 and the wearer's anatomy.

The strap may also comprise an engaging surface 210 similar, for example, to loop in a "hook and loop application" applied to either or both sides of the strap. Alternatively, the strap may be tensioned and secured using Velcro® buckles, snaps, slot buttons, adhesives, or the like The strap 200 should be long enough to reach securely around the appendage and is preferably wide enough to permit comfortable wear. The pad 30 may be attached to the strap using various methods known in the art. The pad 30 may be covered by textile material 40 and secured to the strap body by an attachment mechanism, such as Radio Frequency welding (RF Welding), stitching, adhesives, and the like, and combinations thereof. The textile material 40 is preferably a flexible, elastic material, such as neoprene.

In use, the device is positioned on the wearer (e.g., a human or animal patient) such that the pad 30 is aligned over the anatomy to be compressed. The adjustable strap 200 is then tensioned according to the patient's comfort. The wearer can continue to tighten the strap until the desired compression has been obtained. The fastening mechanism (e.g., buckle, Velcro®) can be engaged before or after the tensioning occurs.

The orthopedic pressure pads of the disclosure can be useful in orthopedic devices for treating lateral epicondylitis ("tennis elbow"), medical epicondylitis ("golfer's elbow"), carpal tunnel syndrome, patellofemoral syndrome (PFS), chondramalacia patella (CMP), chondromalacia, Luxating Patella (commonly referred to as patellar tendonitis), Jumper's knee, and other chronic patellofemoral problems.

For tennis elbow, which occurs at the proximal forearm, the device incorporating the pressure pad is positioned as far up the forearm as possible without interfering with elbow flexion and the perpendicular force contact area is positioned centrally over the extensor compartment forearm musculature.

For golfer's elbow located at the upper forearm or for carpal tunnel syndrome located at the distal forearm, a device including a pressure pad of the current disclosure is positioned as far up the ventral forearm as possible without interfering with elbow flexion and the perpendicular force contact area is positioned centrally with respect to the flexor compartment forearm musculature.

For PFS and CMP, a device including a pressure pad of the current disclosure is positioned at the lower edge of the patella to provide medial and lateral support.

EMBODIMENTS

1. A pressure pad for transferring pressure to an anatomical structure, the pad comprising a base; an interior support comprising a rigid material proximate to the base; a body comprising a soft material projecting outwardly from the base and at least partially enveloping the interior support; a protrusion extending outwardly from the body, at least one geometric feature of the protrusion corresponds to at least one geometric feature of the interior support.

2. The pressure pad of embodiment 1, and further comprising a plurality of protrusions.

3. The pressure pad of embodiment 2, wherein the plurality of protrusions each include a material having a Shore D hardness greater than 35.

4. The pressure pad of embodiment 2, wherein one of the plurality of protrusions includes a material having a Shore D hardness greater than 50.

5. The pressure pad of embodiment 2, wherein the interior support has a Shore D hardness of at least 35 and no greater than 75.

6. The pressure pad of any of the previous embodiments, wherein the interior support is embedded in the body.

7. The pressure pad of any of the previous embodiments, wherein the interior support is not in contact with the base.

8. The pressure pad of any of the previous embodiments and comprising at least three interior supports.

9. The pressure pad of any of the previous embodiments, wherein the corresponding geometric feature includes shape.

10. The pressure pad of any of the previous embodiments, wherein the corresponding features includes height.

11. The pressure pad of any of the previous embodiments, wherein the body has a Shore A hardness of at least 8 and no greater than 30.

12. The pressure pad of any of the previous embodiments, and further comprising a textile disposed on at least a portion of the protrusion and the body.

13. A pressure pad for transferring pressure to an anatomical structure, the pad comprising a base; an interior support comprising a rigid material; a body projecting outwardly from the base and at least partially enveloping the interior support; a protrusion extending outwardly from the body, wherein a shape of the protrusion corresponds with a shape of the interior support.

14. The pressure pad of embodiment 13, wherein the body and the protrusion comprise a soft material.

15. The pressure pad of embodiment 14, wherein the soft material has a Shore A hardness of at least 8 and no greater than 35.

16. The pressure pad of embodiments 13-15, wherein the interior support is coupled to the base.

17. The pressure pad of embodiments 13-15, wherein the interior support is embedded in the body.

18. The pressure pad of embodiments 17, wherein the interior support is not in contact with the base.

19. The pressure pad of embodiments 13-18 and including a plurality of protrusion, each protrusion corresponding to an interior support.

20. The pressure pad of embodiments 13-19, wherein the interior support comprises a pellet of the rigid material fixed in the body.

21. An assembly for transferring pressure to an anatomical structure, the assembly comprising the pressure pad of any of the previous embodiments and a strap securable about a portion of a wearer's anatomy.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the embodiments set forth herein as follows.

What is claimed is:

1. A pressure pad for transferring pressure to an anatomical structure, the pad comprising
    a base;
    an interior support comprising a rigid material proximate to the base;
    a body comprising a soft material projecting outwardly from the base and at least partially enveloping the interior support;
    a protrusion extending outwardly from the body, at least one geometric feature of the protrusion having a shape or height that corresponds to the shape or height, respectively, of at least one geometric feature of the interior support.

2. The pressure pad of claim 1, and further comprising a plurality of protrusions.

3. The pressure pad of claim 2, wherein the plurality of protrusions each include a material having a Shore D hardness greater than 35.

4. The pressure pad of claim 2, wherein one of the plurality of protrusions includes a material having a Shore D hardness greater than 45.

5. The pressure pad of claim 1, wherein the interior support has a Shore D hardness of at least 35 and no greater than 75.

6. The pressure pad of claim 1, wherein the interior support is embedded in the body.

7. The pressure pad of claim 1, wherein the interior support is not in contact with the base.

8. The pressure pad of claim 1 and comprising at least three interior supports.

9. The pressure pad of claim 1, wherein the inner support is disposed between the base and the protrusion.

10. The pressure pad of claim 1, wherein the body has a Shore A hardness of at least 8 and no greater than 30.

11. The pressure pad of claim 1, and further comprising a textile disposed on at least a portion of the protrusion and the body.

12. A pressure pad for transferring pressure to an anatomical structure, the pad comprising
   a base;
   an interior support comprising a rigid material;
   a body projecting outwardly from the base and at least partially enveloping the interior support;
   a protrusion extending outwardly from the body, wherein a shape of the protrusion corresponds with a shape of the interior support.

13. The pressure pad of claim 12, wherein the body and the protrusion comprise a soft material.

14. The pressure pad of claim 13, wherein the soft material has a Shore A hardness of at least 8 and no greater than 35.

15. The pressure pad of claim 12, wherein the interior support is coupled to the base.

16. The pressure pad of claim 12, wherein the interior support is embedded in the body.

17. The pressure pad of claim 16, wherein the interior support is not in contact with the base.

18. The pressure pad of claim 12 and including a plurality of protrusion, each protrusion corresponding to an interior support.

19. The pressure pad of claim 12, wherein the interior support comprises a pellet of the rigid material fixed in the body.

20. An assembly for transferring pressure to an anatomical structure, the assembly comprising a strap securable about a portion of a wearer's anatomy; and a pressure pad attached to the strap, the pad comprising;
   a base;
   a body comprising a soft material projecting outwardly from the base;
   an interior support within the body, the support comprising a rigid material fixed to the base and at least partially enveloping the interior support; and
   a protrusion extending outwardly from the body, wherein the interior support is disposed between the base and the protrusion such that the shape of the protrusion corresponds to the shape of the interior support.

* * * * *

UNITED STATES PATENT AND TRADEMARK OFFICE
CERTIFICATE OF CORRECTION

PATENT NO. : 10,327,977 B2
APPLICATION NO. : 14/406793
DATED : June 25, 2019
INVENTOR(S) : Dominic Julian Page 1 of 1

It is certified that error appears in the above-identified patent and that said Letters Patent is hereby corrected as shown below:

In the Specification

Column 6
Line 51, delete "Epicondylities," and insert -- Epicondylitis, --, therefor.

Column 7
Line 2, after "like" insert -- . --.

Column 7
Line 25, delete "chondramalacia" and insert -- chondromalacia --, therefor.

Signed and Sealed this
Seventh Day of April, 2020

Andrei Iancu
*Director of the United States Patent and Trademark Office*